(12) United States Patent
Fuerst et al.

(10) Patent No.: US 11,266,469 B2
(45) Date of Patent: Mar. 8, 2022

(54) LOCALLY POSITIONED EM TRACKER

(71) Applicant: Verb Surgical Inc., Mountain View, CA (US)

(72) Inventors: Bernhard Adolf Fuerst, Sunnyvale, CA (US); Pablo E. Garcia Kilroy, Menlo Park, CA (US); Berk Gonenc, Cupertino, CA (US); Jose Luis Cordoba, Malaga (ES); Joan Savall, Palo Alto, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 318 days.

(21) Appl. No.: 16/440,844

(22) Filed: Jun. 13, 2019

(65) Prior Publication Data

US 2019/0380809 A1 Dec. 19, 2019

Related U.S. Application Data

(60) Provisional application No. 62/685,821, filed on Jun. 15, 2018.

(51) Int. Cl.
*A61B 34/00* (2016.01)
*A61B 34/30* (2016.01)
(Continued)

(52) U.S. Cl.
CPC ............. *A61B 34/25* (2016.02); *A47C 1/00* (2013.01); *A47C 7/723* (2018.08); *A61B 34/30* (2016.02);
(Continued)

(58) Field of Classification Search
CPC ......... A61B 34/25; A61B 34/30; A61B 34/74; A61B 90/60; A61B 34/37; A61B 90/37;
(Continued)

(56) References Cited

U.S. PATENT DOCUMENTS 6,839,595 B2 * 1/2005 Tepper ..................... A61N 2/02
600/14
8,831,782 B2 * 9/2014 Itkowitz .................. A61B 34/35
700/264
(Continued)

FOREIGN PATENT DOCUMENTS

EP 2671686 B1 5/2016
WO WO-2019220409 A1 * 11/2019 ............. A61B 34/37

OTHER PUBLICATIONS

International Preliminary Report on Patentability for International Application No. PCT/US2019/037226 dated Dec. 24, 2020, 9 pages.
(Continued)

*Primary Examiner* — Jaime Figueroa
(74) *Attorney, Agent, or Firm* — Womble Bond Dickinson (US) LLP

(57) ABSTRACT

A user console for a surgical robotic system has a seat having an armrest and an electromagnetic (EM) transmitter coupled to the armrest to generate an EM field in an EM tracking space around the armrest. A user input device having a handheld housing is to be positioned within the EM tracking by an operator who is seated in the seat, during a surgical procedure. Other aspects are also described and claimed.

12 Claims, 2 Drawing Sheets

(51) Int. Cl.
  *B25J 13/08* (2006.01)
  *A61B 34/20* (2016.01)
  *A61B 34/37* (2016.01)
  *A61B 90/00* (2016.01)
  *A61B 90/60* (2016.01)
  *A47C 7/72* (2006.01)
  *A47C 1/00* (2006.01)

(52) U.S. Cl.
  CPC .............. *A61B 34/37* (2016.02); *A61B 34/74* (2016.02); *A61B 90/37* (2016.02); *A61B 90/60* (2016.02); *B25J 13/087* (2013.01); *A61B 2034/2048* (2016.02); *A61B 2034/2051* (2016.02); *A61B 2034/2057* (2016.02); *A61B 2090/3937* (2016.02)

(58) Field of Classification Search
  CPC .... A61B 2090/0937; A61B 2034/2051; A61B 2034/2057; A61B 2034/2048; A61B 2017/00212; A47C 7/723; A47C 1/00; B25J 13/087; G06F 3/03547; G06F 3/0346
  USPC .......................................................... 700/264
  See application file for complete search history.

(56) References Cited

U.S. PATENT DOCUMENTS

| | | | | |
|---|---|---|---|---|
| 10,568,703 B2* | 2/2020 | Nobles | ................... | A47B 21/02 |
| 2002/0188193 A1* | 12/2002 | Biglieri | ................... | A61B 8/00 |
| | | | | 600/411 |
| 2003/0144590 A1* | 7/2003 | Maschke | ................ | A61B 5/065 |
| | | | | 600/425 |
| 2003/0171678 A1* | 9/2003 | Batten | ................... | A61B 8/4254 |
| | | | | 600/443 |
| 2004/0236541 A1* | 11/2004 | Kramer | ................... | G06T 19/20 |
| | | | | 703/1 |
| 2007/0285386 A1 | 12/2007 | Lim et al. | | |
| 2011/0118748 A1* | 5/2011 | Itkowitz | ................. | A61B 34/37 |
| | | | | 606/130 |
| 2012/0071892 A1* | 3/2012 | Itkowitz | ................. | B25J 9/1612 |
| | | | | 606/130 |
| 2012/0316681 A1 | 12/2012 | Hagn et al. | | |
| 2014/0018960 A1* | 1/2014 | Itkowitz | ................. | A61B 90/98 |
| | | | | 700/264 |
| 2017/0042625 A1 | 2/2017 | Sartor | | |
| 2017/0102772 A1 | 4/2017 | Hesch et al. | | |
| 2017/0307891 A1 | 10/2017 | Bucknor et al. | | |
| 2018/0036088 A1 | 2/2018 | Kilroy et al. | | |
| 2018/0078319 A1* | 3/2018 | Nobles | ..................... | B25J 13/02 |
| 2018/0092706 A1* | 4/2018 | Anderson | .............. | A61B 90/37 |

OTHER PUBLICATIONS

Goh, A.H.W., et al. "Interactive PTZ Camera Control System Using Wii Remote and Infrared Sensor Bar", World Academy of Science, Engineering, and Technology 46, 2008, pp. 127-132.

Olson, Edwin, "AprilTag: A robust and flexible visual fiducial system", IEEE International Conference on Robotics and Automation, May 9, 2011, 8 pages.

Yaniv, Ziv, et al., "Electromagnetic tracking in the clinical environment", Med. Phys. 36 (3), Mar. 2009, pp. 876-892.

International Search Report and Written Opinion dated Oct. 8, 2019, Application No. PCT/US2019/037226.

Extended European Search Report from related European Patent Application No. 19818641.3 dated Dec. 23, 2021, 7 pages.

* cited by examiner

LOCALLY POSITIONED EM TRACKER

This non-provisional patent application claims the benefit of the earlier filing date of U.S. provisional application No. 62/685,821 filed Jun. 15, 2018.

FIELD

Embodiments related to robotic systems are disclosed. More particularly, embodiments related to surgical robotic systems and corresponding user input devices are disclosed.

BACKGROUND INFORMATION

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon operator to control a robotically-assisted tool located at an operating table. The surgeon may use a computer console located in the operating room, or it may be located in a different city, to command a robot to manipulate the surgical tool mounted on the operating table. The robotically-controlled surgical tool can be a grasper mounted on a robotic arm. Accordingly, the surgical robotic system may be controlled by the remote surgeon to grasp tissue during a robotic surgery.

Control of the surgical robotic system may require control inputs from the surgeon. For example, the surgeon may hold in her hand a user input device, UID, such as a joystick or a computer mouse that she manipulates to generate the signals based on the system produces control commands that control motion of the surgical robotic system components, e.g., an actuator, a robotic arm, and/or a surgical tool of the robotic system. In this manner, the pose of the surgical tool will mimic and follow the pose of the UID.

SUMMARY

In order for the surgical tool to mimic and follow the pose of the UID, the surgical robotic system needs to accurately measure the pose (position and orientation) of the UID. In an electromagnetic tracker, EM tracker, a modulated magnetic field generated in the workspace of the surgeon operator establishes a reference which is measured by a sensor that is fixed in the UID. In the case of medical applications, movements in the sub-millimeter (for translation) and sub-degree (for orientation) range may be required to achieve clinically feasible operation. It is noted that system noise, which can lead to control errors, may be reduced by filtering the spatial state signal from the UID. Signal filtering however can introduce latency that has associated undesirable effects on the stable operation of the robotic end effector or surgical tool. Accordingly, a noise-free, accurate, and real-time sensing methodology is needed to detect the status, position, and orientation of the UID used for the control of surgical robotic systems.

An embodiment of the invention is a user console for a surgical robotic system that has a seat having an armrest and an electromagnetic (EM) transmitter coupled to the armrest to generate an EM field in an EM tracking space around the armrest. This allows the UID to be in the sweet spot of the EM tracker.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments of an electromagnetic tracker (EM tracker) for tracking the pose of a user input device (UID) for controlling a surgical robotic system are described. The EM tracker in some cases could also be used to control other medical systems, such as interventional cardiology systems or medical vision systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from an operator. Similarly, "proximal" may indicate a location in a second direction opposite to the first direction, e.g., toward the operator. Such terms are provided to establish relative frames of reference, however, and are not intended to limit the use or orientation of a UID to a specific configuration described in the various embodiments below.

Figure 1:
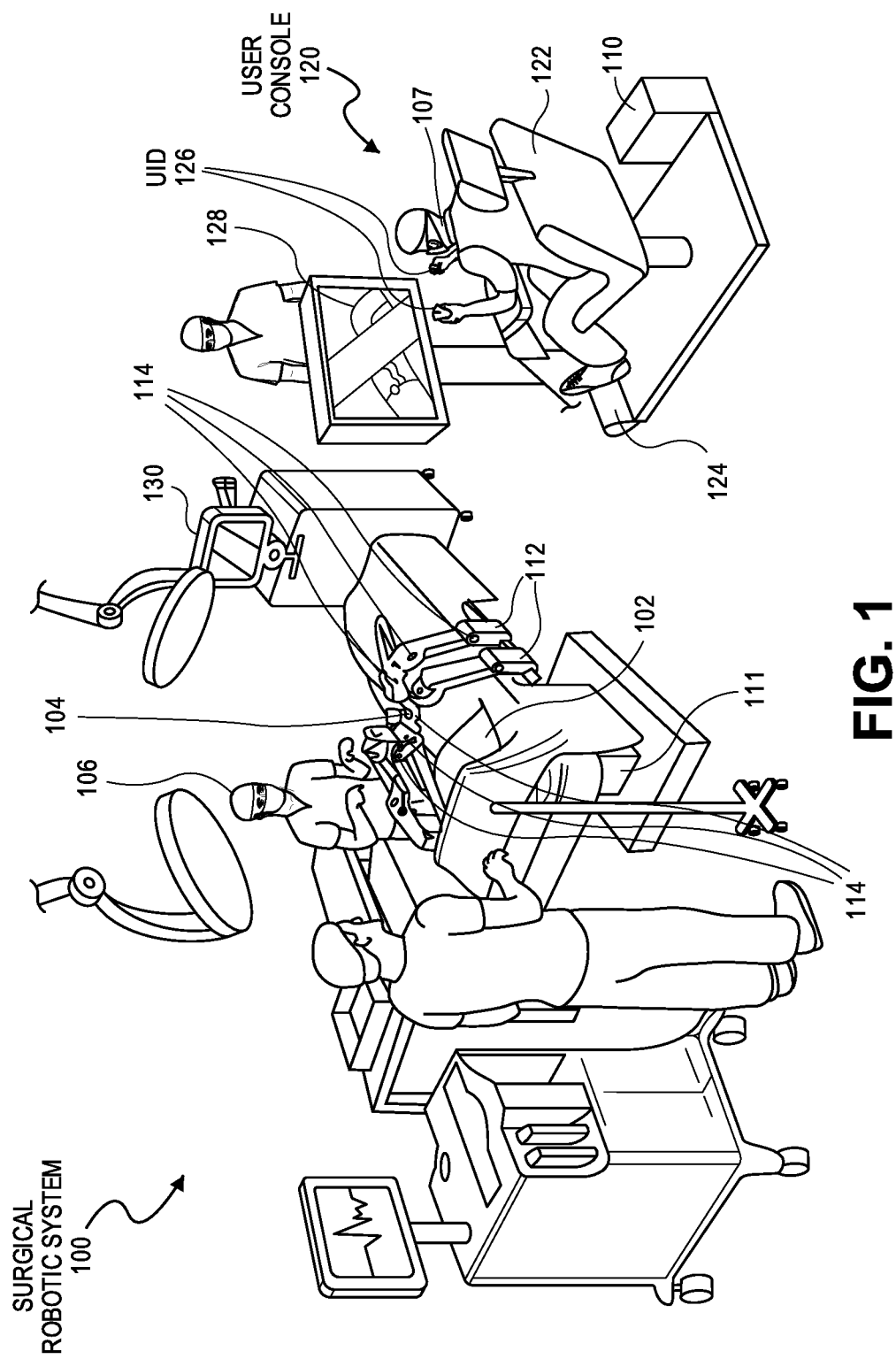
FIG. 1 is a pictorial view of an example surgical robotic system in an operating arena, in accordance with an embodiment.

FIG. 1 is a pictorial view of an example surgical robotic system 100 in an operating arena. The robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be an end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be controlled manually, by a bedside operator 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user input devices, UIDs 126, and at least one operator display 128 configured to display, for example, a view of the surgical site inside patient 102. In the example user console 120, remote operator 107 is sitting in seat 122 and viewing the operator display 128 while manipulating a foot-operated control 124 and a handheld UID 126 in order to remotely control the arms 112 and surgical tools 104 (that are mounted on the distal ends of the arms 112). Foot-operated control(s) 124 can be foot pedals, such as seven pedals, that generate motion control signals when actuated. User console 120 may include one or more additional input devices, such as a keyboard or a joystick, to receive manual inputs to control operations of user console 120 or surgical robotic system 100. The operator 107 may hold the UID 126 between several fingers of her hand, while being able to freely move the UID 126 as a whole within a workspace. The workspace may be a range of arms reach of the operator. The UID 126 may be unrestricted by mechanical linkages that constrain a size of the workspace (also referred to here as an ungrounded UID).

In some variations, bedside operator 106 may also operate system 100 in an "over the bed" mode, in which bedside operator 106 is now at a side of patient 102 and is simultaneously manipulating a robotically-driven tool (end effector attached to arm 112), e.g., with a handheld UID 126 held in one hand, and a manual laparoscopic tool. For example, the bedside operator's left hand may be manipulating the handheld UID 126 to control a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion, and administered anesthesia. Initial access to the patient anatomy can be achieved using known techniques, such as by forming an incision in the skin. A trocar and/or other surgical tool can be inserted into the incision through the optical entry in the patient. The trocar can then be positioned at the surgical site. Initial access to the surgical site may be performed manually while the arms of the robotic system 100 are in a stowed configuration or withdrawn configuration (to facilitate access to the surgical site) or in an operator-defined parking pose. Once initial access is completed, initial positioning or preparation of the robotic system including its arms 112 may be performed. Next, the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Robotic system 100 may produce control signals as a function of the spatial state signals, to control proportional motion of actuator 114. In one embodiment, a console processor of console computer system 110 receives the spatial state signals and generates the corresponding control signals. Based on these control signals, which control how the actuator 114 is energized to move a segment or link of arm 112, the movement of a corresponding surgical tool including an end effector that is attached to the arm may mimic the movement of UID 126. Similarly, interaction between remote operator 107 and UID 126 can generate, for example, a grip control signal that causes a jaw of a grasper of the surgical tool to close and grip the tissue of patient 102.

The sensed motion of UID 126 may alternatively be provided to control other aspects of surgical robotic system 100. For example, gestures detected by a finger clutch may generate a clutch signal to pause the motion of actuator 114 and the corresponding surgical tool 104. For example, when an operator touches the finger clutch of UID 126 with a finger, the finger clutch may generate a clutch signal, and the clutch signal may be an input signal to pause the motion of actuator 114. Similarly, one or more capacitive sensing pads may be located on UID 126, and the operator may touch the capacitive sensing pads to control a camera view of an endoscope, a cursor on a display of user console 120, etc., while performing a diagnostic, surgical, laparoscopic, or minimally invasive surgical procedure, or another robotic procedure.

Surgical robotic system 100 may include several UIDs 126 where respective control signals are generated for each UID that control the actuators and the surgical tool (end effector) of a respective arm 112. For example, remote operator 107 may move a first UID 126 to control the motion of actuator 114 that is in a left robotic arm, where the actuator responds by moving linkages, gears, etc., in that arm 112. Similarly, movement of a second UID 126 by remote operator 107 controls the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors that are controlled so that they drive the rotation of a joint of arm 112, to for example change, relative to the patient, an orientation of an endoscope or a grasper of the surgical tool that is attached to that arm. Motion of several actuators 114 in the same arm 112 can be controlled by the spatial state signals generated from a particular UID 126. UIDs 126 can also control motion of respective surgical tool graspers. For example, each UID 126 can generate a respective grip signal to control motion of an actuator, e.g., a linear actuator that opens or closes jaws of the grasper at a distal end of the surgical tool to grip tissue within patient 102.

In some aspects, the communication between platform 111 and user console 120 may be through a control tower 130, which may translate operator commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
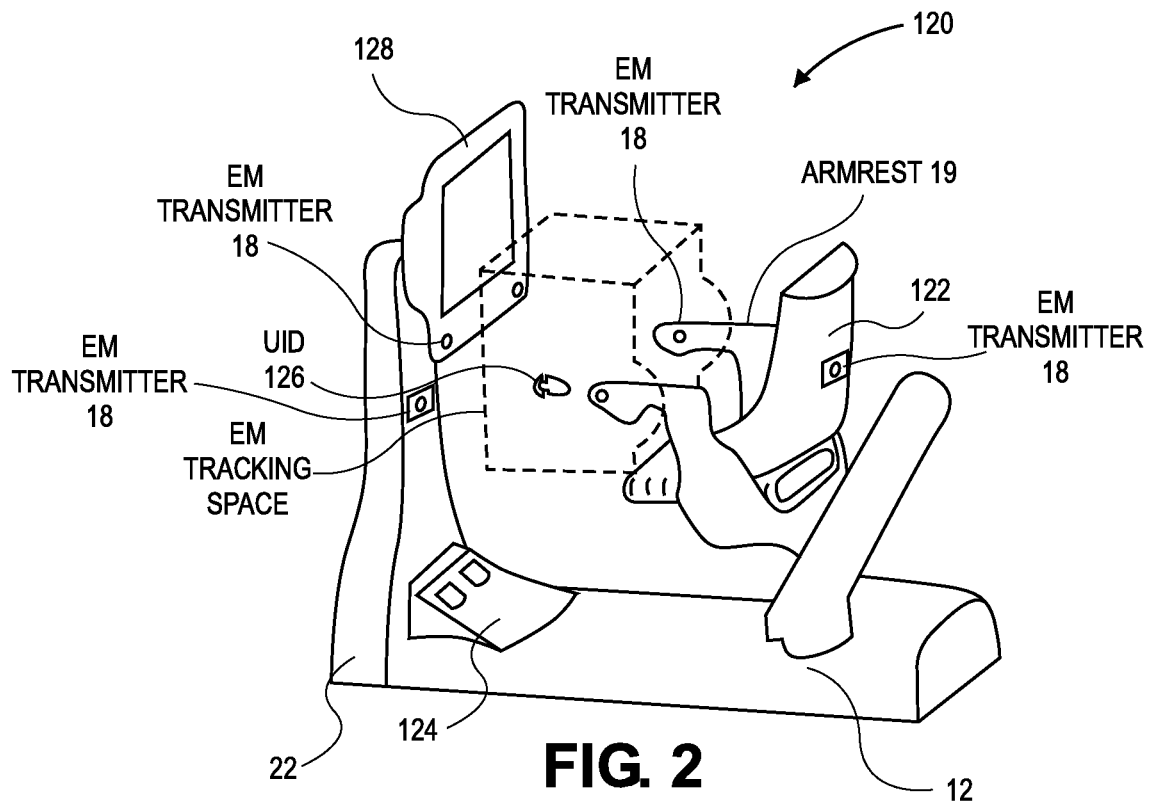
FIG. 2 is a perspective view of a user console, in accordance with an embodiment.

Referring to FIG. 2, a perspective view of an example of the user console 120 is shown in accordance with an embodiment. As described above, the UID 126 can include an electromagnetic sensor (EM sensor, not shown) that interacts with an electromagnetic field (EM field) of the workspace of the operator 107 to generate a spatial state signal. More particularly, the EM field can be generated by one or more EM transmitters 18 located on or around the user console 120, and is present within an EM tracking space or volume for example as see in FIG. 2.

The user console 120 can include a base 12 to support the seat 122 and a stand 22 to support the display 128 of the surgical robotic system, as shown. In one embodiment, the base 12 or the stand 22 also supports the foot-operated controls 124. The remote operator 120 may sit on the generally horizontal seat portion of the seat 122, while viewing the display 128 during a surgical procedure and holding the UID 126 in her hand. The user console 120 can include a tracking subsystem to monitor movement of the UID 126. For example, the tracking subsystem may be an EM tracking subsystem or EM tracker, having an EM source, a UID-mounted EM sensor, and processing electronics (e.g., part of the console computer system 110) that prepares a spatial state signal that may originate from the UID-mounted EM sensor (e.g., digitizes and filters a sensor output signal of the EM sensor.) The spatial state signal monitors movement of the UID 126, which is associated with one of the arms 112 (e.g., a separate UID is associated with each surgical robotic arm 112.) The EM source can generate an EM field in an EM tracking space, while the remote operator 107 is holding the UID 126 within the EM tracking space as shown. The EM tracking space may be the workspace within which the remote operator 107 moves the UID 126 while held in her hand, to generate the spatial state signal. The EM tracking space is thus said to be in front of the backrest portion of the seat 122, and more specifically in front of the operator 107 when seated in the seat 122. A digital control system (e.g., a microelectronic processor that is executing instructions stored in memory as part of the surgical robotic system, for instance in the control tower 130) generates control commands to drive various actuators 114 in the robotic arm 112. These control commands are responsive to the spatial state signal produced by the EM tracking subsystem (that originates from the UID 126 that is associated with the particular arm 112.) The control commands are generated in accordance with a digital control algorithm and are designed to drive the actuators 114 to cause a corresponding movement of the surgical tool 104 that is attached to the associated arm 112 (during the surgical procedure.)

The user console 120 may include a source of an electromagnetic field used by the EM tracking subsystem to track the pose of the UID 126. The source can be one or more EM transmitters 18 used as a field generator to generate a position varying magnetic field that establishes a coordinate space or frame of reference. The EM transmitter(s) 18 can generate the electromagnetic field within the EM tracking space.

In an embodiment, the seat 122 of the user console includes an armrest 19. One or more EM transmitters 18 can be integrated with the armrest 18 as shown. For example, an EM transmitter may be mounted on the armrest 19 to generate the EM tracking space around the armrest. The operator 107 will typically hold the UID 126 in her hand and therefore near the distal end of the armrest 19 while seated, where the distal end is the free end of the armrest 19 that is furthest from the seated operator 107 and the proximal end is the opposite end which is attached to the seat 122 or the base and is closest to the seated operator 107. As a result, the EM field is localized so that the UID 126 will mostly remain in a sub-volume (of the EM tracking space) that is associated with or yields the lowest tracking error from the EM tracking subsystem. More particularly, the EM tracking space exhibits good quality within a spherical field portion existing around the distal end of the armrest, and thus, the UID that is held in that spherical field (near the distal end of the armrest) may have improved tracking quality due to a low proximity between the EM sensor that is inside the UID 126 and the EM transmitters 18 that generate the EM field.

The EM tracking sensor that is a housing of the UID 126 can be a magnetic tracking probe capable of measuring 6 degrees of freedom within the EM tracking space. The EM sensor can be a sensor containing coils in which current is induced via the electromagnetic field produced by the EM transmitter 18 in the EM tracking space. The tracking sensor can have a known response to the electromagnetic field, and the response may be measured as an electrical signal across the coils of the EM sensor. By interpreting such coil signal behavior, a position and orientation of the EM sensor, and thus the pose of the UID, can be determined. The measured response of the EM sensor may be output to the console computer system as the EM spatial state signal representing movement of the UID within the EM tracking space.

The seat 122 can include several EM transmitters 18. For example, the seat may have a second armrest, and a second EM transmitter may be mounted on the second armrest as shown in FIG. 2. The second EM transmitter can generate a field in a second EM tracking space around the second armrest. The transmitter 18 in the left armrest 18 produces a left EM tracking space in which a UID 126 is positioned in the left hand of the operator 107 (while seated), while the transmitter in the right armrest produces a right EM tracking space in which another UID 126 is positioned in the right hand of the seated operator 107. Accordingly, several EM tracking sub volumes with low tracking errors can be localized to the areas where each of several UIDs are held, respectively, during the surgical operation.

In another embodiment, the EM tracking space (field) shown in FIG. 2 is produced by an EM transmitter 18 that is located in a seat back (or backrest) portion of the seat 122, as also shown in FIG. 2. That figure also shows another embodiment where the EM tracking space shown is produced by an EM transmitter 18 that is mounted in the horizontal seat portion (on which the buttocks of the operator 107 are resting during the surgery procedure.) Yet another embodiment depicted in FIG. 2 is one in which the EM tracking space is produced by an EM transmitter 18 that is mounted to the stand 12 at a position below the operator display 128, at a height above the ground (on which the base 12 or the stand 22 rests) that is closer to the bottom of the display 128 than to the ground. Still another embodiment is shown in FIG. 2, where a pair of transmitters 18 are mounted at the bottom of the operator display 128 (below the main view screen of the display 128), one to the left of a center line and another to the right, that produce the EM tracking space.

Figure 3:
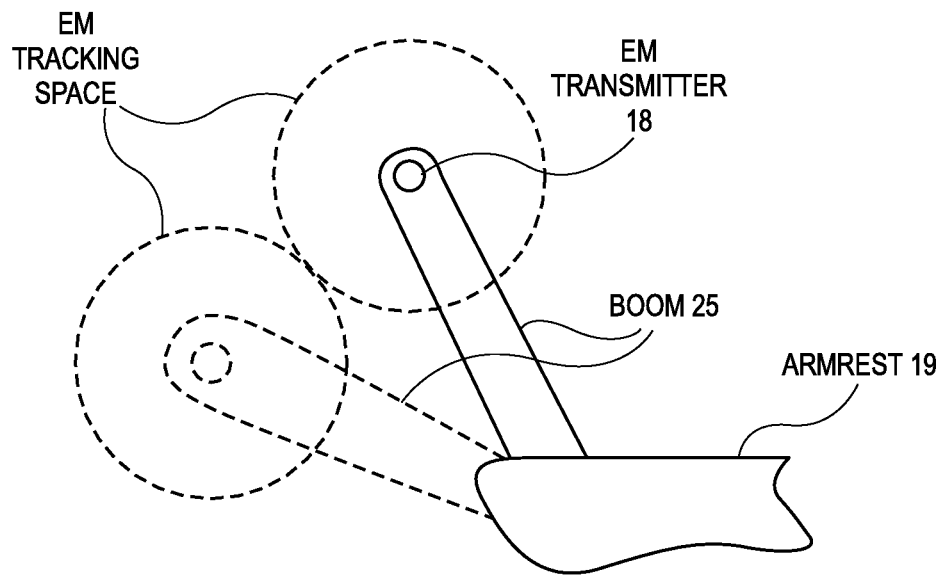
FIG. 3 is a side view of a user console armrest including a movable electromagnetic transmitter, in accordance with an embodiment.

Referring to FIG. 3, a side view of another example user console armrest 19 is shown, including a movable EM transmitter 18 in accordance with an embodiment. Here, the EM transmitter 18 is mounted on a movable structure that moves relative to the armrest 19. For example, the user console 120 can include a boom 25 that is pivotally connected to the armrest 19 and on which the EM transmitter 18 is mounted as shown. More particularly, the boom 25 can be connected to the distal end of the armrest 19 such that a distal end of the boom 25 can follow an arc around the distal end of the armrest. The EM transmitter 18 can be mounted on the boom 25, e.g., near the distal end of the boom. The EM transmitter can generate the EM tracking space around the distal end of the boom.

In an embodiment, the operator 107 can adjust the boom to a position that moves the EM tracking space to a location that coincides with the UID. For example, if the operator prefers to rest his forearms on the armrest during the surgical operation, the boom can be rotated downward to the location indicated by dotted lines such that the EM tracking space coincides with the UID in front of the distal end of the armrest, as in FIG. 3. Accordingly, the operator can adjust the EM tracking space envelope to cover a region where the UID is held. This allows the UID to be in the sweet spot of the EM tracker. In an alternative embodiment, the movable EM transmitter may be located on another component of the user console. For example, the boom may be connected to the base 12 or the display 128 of the user console 120. The boom can pivot about a connection point, e.g., move in an arc relative to the display. Similarly, the boom may have a telescoping mechanism to allow the EM transmitter to move axially (in a longitudinal direction) relative to the base component or the connection point. Accordingly, the EM transmitter can be moved to a preferred location to generate a localized EM field for UID tracking.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A user console for a surgical robotic system, comprising:
    a seat having an armrest; and
    a first electromagnetic (EM) transmitter that is part of an EM tracking subsystem and is configured to generate a first EM field in a first tracking space, wherein the first EM transmitter is mounted on a free end of the armrest such that the first EM field is localized around the free end of the armrest.

2. The user console of claim 1, wherein the seat includes a second armrest, and further comprising a second EM transmitter mounted on the second armrest to generate a second EM field in a second EM tracking space around the second armrest.

3. The user console of claim 1 further comprising a boom mounted on the armrest, wherein the boom is movable relative to the armrest, and wherein the first EM transmitter is mounted on the boom.

4. The user console of claim 1 further comprising:
    a user input device, UID, having a housing and an EM sensor within the housing, wherein the EM sensor is to produce a spatial state signal in six degrees of freedom that is responsive to the first EM field in the first tracking space while the UID is being held in a hand of an operator and is located within the first tracking space.

5. The user console of claim 4 wherein the UID is an ungrounded UID.

6. A user console for a surgical robotic system, comprising:
    a seat having a seat portion and backrest portion; and
    an electromagnetic (EM) transmitter that is part of an EM tracking subsystem, wherein the EM transmitter is mounted on the backrest portion behind the seat portion and is configured to generate an EM field in a tracking space in front of the seat portion.

7. The user console of claim 6 further comprising:
    a user input device, UID, having a housing and an EM sensor within the housing, wherein the EM sensor is to produce a spatial state signal in six degrees of freedom that is responsive to the EM field in the tracking space while the UID is being held in a hand of an operator sitting between the backrest portion and the tracking space.

8. A user console for a surgical robotic system, comprising:
    a seat;

a display;

a stand on which the display is supported; and an electromagnetic (EM) transmitter that is part of an EM tracking subsystem, and is mounted on the stand to generate an EM field in a tracking space in front of the seat.

9. The user console of claim 8 wherein the EM transmitter is positioned at a height above the ground on which the stand is to rest that is closer to the bottom of the display than to the ground.

10. The user console of claim 8 further comprising:

a user input device, UID, having a housing and an EM sensor within the housing, wherein the EM sensor is to produce a spatial state signal in six degrees of freedom that is responsive to the EM field in the tracking space while the UID is being held in a hand of an operator and is located within the tracking space.

11. A user console for a surgical robotic system, comprising:

a seat;

a display; and an electromagnetic (EM) transmitter that is part of an EM tracking subsystem, and is mounted on the display to generate an EM field in a tracking space in front of the seat.

12. The user console of claim 11 wherein the EM transmitter is mounted closer to the bottom of the display than to the top of the display.

\* \* \* \* \*

UNITED STATES PATENT AND TRADEMARK OFFICE
CERTIFICATE OF CORRECTION

| | |
|---|---|
| PATENT NO. | : 11,266,469 B2 |
| APPLICATION NO. | : 16/440844 |
| DATED | : March 8, 2022 |
| INVENTOR(S) | : Bernhard Adolf Fuerst |

It is certified that error appears in the above-identified patent and that said Letters Patent is hereby corrected as shown below:

In the Claims

Under Column 8, at Line 33, please delete "a second EM tracking space" and insert -- a second tracking space --

Signed and Sealed this
Sixth Day of September, 2022

*Katherine Kelly Vidal*

Katherine Kelly Vidal
*Director of the United States Patent and Trademark Office*